(12) United States Patent
Paspa et al.

(10) Patent No.: US 10,441,777 B2
(45) Date of Patent: Oct. 15, 2019

(54) IMPLANTABLE MEDICAL DEVICE HAVING RESTRAINED TETHER DEVICE

(71) Applicant: NANOSTIM, INC., Sunnyvale, CA (US)

(72) Inventors: Paul Paspa, Los Gatos, CA (US); Joseph Ramon Callol, San Mateo, CA (US); Thomas B. Eby, Mountain View, CA (US)

(73) Assignee: Pacesetter, Inc., Sylmar, CA (US)

( * ) Notice: Subject to any disclaimer, the term of this patent is extended or adjusted under 35 U.S.C. 154(b) by 714 days.

(21) Appl. No.: 14/481,799

(22) Filed: Sep. 9, 2014

(65) Prior Publication Data

US 2016/0067447 A1  Mar. 10, 2016

(51) Int. Cl.
*A61N 1/05* (2006.01)
*A61N 1/375* (2006.01)
*A61B 17/34* (2006.01)
*A61N 1/372* (2006.01)

(52) U.S. Cl.
CPC ............ *A61N 1/05* (2013.01); *A61B 17/3468* (2013.01); *A61N 1/3756* (2013.01); *A61N 1/37205* (2013.01); *A61N 2001/058* (2013.01)

(58) Field of Classification Search
CPC .. A61N 1/05; A61N 1/37205; A61B 17/3468; A61B 2017/347; A61B 2017/12077; A61B 2017/00464; A61B 2017/00473; A61B 2017/2931; A61F 2/2433; A61F 2/958–2002/9586
USPC ........................................................ 606/127
See application file for complete search history.

(56) References Cited

U.S. PATENT DOCUMENTS

| | | | | |
|---|---|---|---|---|
| 4,744,366 A | * | 5/1988 | Jang | A61M 25/1011 604/101.02 |
| 5,226,889 A | * | 7/1993 | Sheiban | A61F 2/958 604/103.1 |
| 5,669,924 A | * | 9/1997 | Shaknovich | A61F 2/07 604/101.04 |
| 6,059,719 A | * | 5/2000 | Yamamoto | A61B 1/00059 600/104 |
| 6,149,664 A | * | 11/2000 | Kurz | A61B 17/12022 606/108 |
| 6,770,092 B2 | * | 8/2004 | Richter | A61F 2/07 623/1.11 |
| 7,445,610 B2 | * | 11/2008 | Adams | A61F 2/856 604/96.01 |
| 8,377,044 B2 | * | 2/2013 | Coe | A61B 17/00234 606/1 |
| 9,539,423 B2 | * | 1/2017 | Bonner | A61N 1/0592 |

(Continued)

OTHER PUBLICATIONS

Non-Final Office Action dated Dec. 27, 2017; Related U.S. Appl. No. 14/481,818.

*Primary Examiner* — Elizabeth Houston
*Assistant Examiner* — Charles M Wei
(74) *Attorney, Agent, or Firm* — Theresa Raymer

(57) ABSTRACT

A system for implanting an implantable medical device (IMD) within a patient may include an IMD including an attachment member, and a delivery catheter including at least one tethering device having at least a portion positioned within a restrainer. The tethering device(s) is configured to removably tether to the attachment member of the IMD. The restrainer is configured to maintain the tethering device(s) in alignment along a delivery path of the delivery catheter.

14 Claims, 12 Drawing Sheets

(56) References Cited

U.S. PATENT DOCUMENTS

| | | | |
|---|---|---|---|
| 2006/0105613 A1* | 5/2006 | Carroll | H01R 13/582 439/404 |
| 2007/0219611 A1* | 9/2007 | Krever | A61F 2/954 623/1.11 |
| 2008/0243106 A1* | 10/2008 | Coe | A61B 17/00234 606/1 |
| 2011/0270340 A1 | 11/2011 | Pellegrini | |
| 2012/0095539 A1 | 4/2012 | Khairkhahan | |
| 2012/0165827 A1* | 6/2012 | Khairkhahan | A61N 1/362 606/129 |
| 2012/0197373 A1* | 8/2012 | Khairkhahan | A61N 1/3756 607/127 |
| 2013/0012925 A1 | 1/2013 | Berthiaume | |
| 2014/0074114 A1* | 3/2014 | Khairkhahan | A61N 1/3756 606/129 |
| 2014/0277351 A1* | 9/2014 | Ridgley | A61F 2/958 623/1.11 |
| 2017/0113035 A1 | 7/2017 | Bonner | |

\* cited by examiner

IMPLANTABLE MEDICAL DEVICE HAVING RESTRAINED TETHER DEVICE

BACKGROUND

Embodiments of the present disclosure generally relate to implantable medical devices, and, more particularly, to systems and methods for implanting a medical device.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like. Implantable medical devices (hereafter generally "implantable medical devices" or "IMDs") are configured to be implanted within patient anatomy and commonly employ one or more leads with electrodes that either receive or deliver voltage, current or other electromagnetic pulses (generally "energy") from or to an organ or tissue for diagnostic or therapeutic purposes.

Typically, an intra-cardiac IMD is introduced into the heart through a catheter. In general, an IMD may be connected to a catheter in a docked state, in which the IMD is securely attached to the catheter. In the docked state, the catheter may be operated to guide the IMD to an implant site. Once the IMD is proximate to the implant site, the delivery system may be used to torque the IMD into patient tissue.

Once the IMD is secured into patient tissue, the IMD may be moved into a tethered state with respect to the delivery system. In the tethered state, the delivery system separates from the IMD, but remains connected thereto. In one known system and method, two separate and distinct tethers connect the IMD to the catheter in the tethered stated. In the tethered state, an implanting physician may test the IMD to make sure that the IMD is securely and electrically connected to patient tissue at a desired location. If the physical and/or electrical connection between the IMD and the patient tissue is less than optimal, the IMD may be re-docked to the catheter so that that the IMD may be moved to a better position for implantation.

Once the implanting physician is satisfied with the location of the IMD within patient anatomy, the IMD is transitioned from the tethered state to a release state. During the release state, the IMD disconnects from the catheter.

As noted above, in the tethered state, two tethers may connect the IMD to the catheter. Each tether may include a distal tethering member, such as a bump, sphere, stud or the like. The tethering members are typically secured to an attachment feature of the IMD. In order to release the tethers from the attachment feature, the tethers are misaligned with one another so that a combined diameter of the distal ends of the tethers is smaller than a hole formed through the attachment feature. In this manner, both the tethers may be removed from the attachment feature by sliding them out of the hole.

However, known systems and methods may be susceptible to inadvertent release. That is, the tethers may inadvertently pass through the hole of the attachment feature during implantation before the implanting physician desires to release the IMD from the catheter. For example, if during the tethered state the IMD moves out of axial alignment with a distal end of the catheter, the two tethers may become staggered with respect to one another as the tethering lines splay away from one another. As such, the tethering members at the distal ends of the tethering lines may misalign with one another, and the tension within the tethering lines may cause the tethering members to retreat out of the hole within the attachment feature, thereby releasing the IMD from the catheter. As such, the IMD may be inadvertently released from the catheter when an implanting physician still desires to test the IMD in a tethered state. Also, the tethers may become entangled with one another.

SUMMARY

Certain embodiments provide a system for implanting an implantable medical device (IMD) within a patient. The system may include an IMD including an attachment member, and a delivery catheter including at least one tethering device having at least a portion positioned within a restrainer. The tethering device(s) is configured to removably tether to the attachment member of the IMD. The restrainer is configured to maintain the tethering device(s) in alignment along a delivery path of the delivery catheter. The restrainer limits outward movement of the tethering device(s) in relation to the delivery path.

In at least one embodiment, the delivery catheter includes a catheter shaft. The restrainer is moveably positioned within the catheter shaft.

In at least one embodiment, the restrainer may include a main body having an inner diameter that defines a central passage. At least a portion of the tethering device(s) is positioned within the central passage.

The restrainer may exert an inwardly-directed force into at least a portion of the tethering device(s). For example, the restrainer may exert a compressive force into at least a portion of the tethering device(s).

In at least one embodiment, the restrainer encapsulates at least a distal portion of the tethering device(s). The restrainer may extend from a proximal end of the tethering device(s) to a distal end of the tethering device(s). In at least one other embodiment, the restrainer extends over a portion of the tethering device(s) that is configured to outwardly extend from the delivery catheter.

The at least one tethering device may include first and second tethers having first and second distal tethering members. In at least one other embodiment, the at least one tethering device includes a first tethering device having a distal protuberance, and a second tethering device having a featureless elongated distal segment. In at least one other embodiment, the at least one tethering device include a tethering snare.

DETAILED DESCRIPTION

Embodiments of the present disclosure provide systems and methods of restricting, restraining, or otherwise limiting movement of tether devices of a delivery catheter along a delivery, advancing, or tethering path of a delivery catheter. For example, a restrainer may ensure that the tethering devices remain aligned with a delivery path of the delivery catheter. Certain embodiments of the present disclosure provide a restrainer, such as a flexible lumen, tube, sleeve, sheath, cable, or the like, that is positioned around at least portions of the tethers to maintain the tethers in an orientation that may generally be aligned with a direction that is parallel with a delivery, advancing, or tethering direction of a delivery catheter. The restrainer may be formed of various materials, such as elastomeric materials, latex, polymide, polyethylene, terephthalate, or other thin-walled metallic tubing such as nitinol. Embodiments of the present disclosure prevent or otherwise reduce the possibility of the tethers bowing, splaying away, separating, or otherwise moving away from one another.

The IMD may be any one of various types of implantable devices, such as, for example, an implantable pacemaker, implantable cardioverter-defibrillator ("ICD"), defibrillator, cardiac rhythm management ("CRM") device, neurostimulator, or the like. In at least one embodiment, the IMD may include a leadless cardiac pacemaker that may be enclosed in a hermetic housing or can that may be positioned on the inside or outside of a cardiac chamber. The pacemaker may have two or more electrodes located within, on, or near the housing, for delivering pacing pulses to muscle of the cardiac chamber and optionally for sensing electrical activity from the muscle, and for bidirectional communication with at least one other device within or outside the body. The housing may contain a primary battery to provide power for pacing, sensing, and communication, for example bidirectional communication. The housing may optionally contain circuits for sensing cardiac activity from the electrodes. The housing may contain circuits for receiving information from at least one other device via the electrodes and may contain circuits for generating pacing pulses for delivery via the electrodes. The housing may optionally contain circuits for transmitting information to at least one other device via the electrodes and may optionally contain circuits for monitoring device health. The housing may contain circuits for controlling these operations in a predetermined manner.

Figure 1:
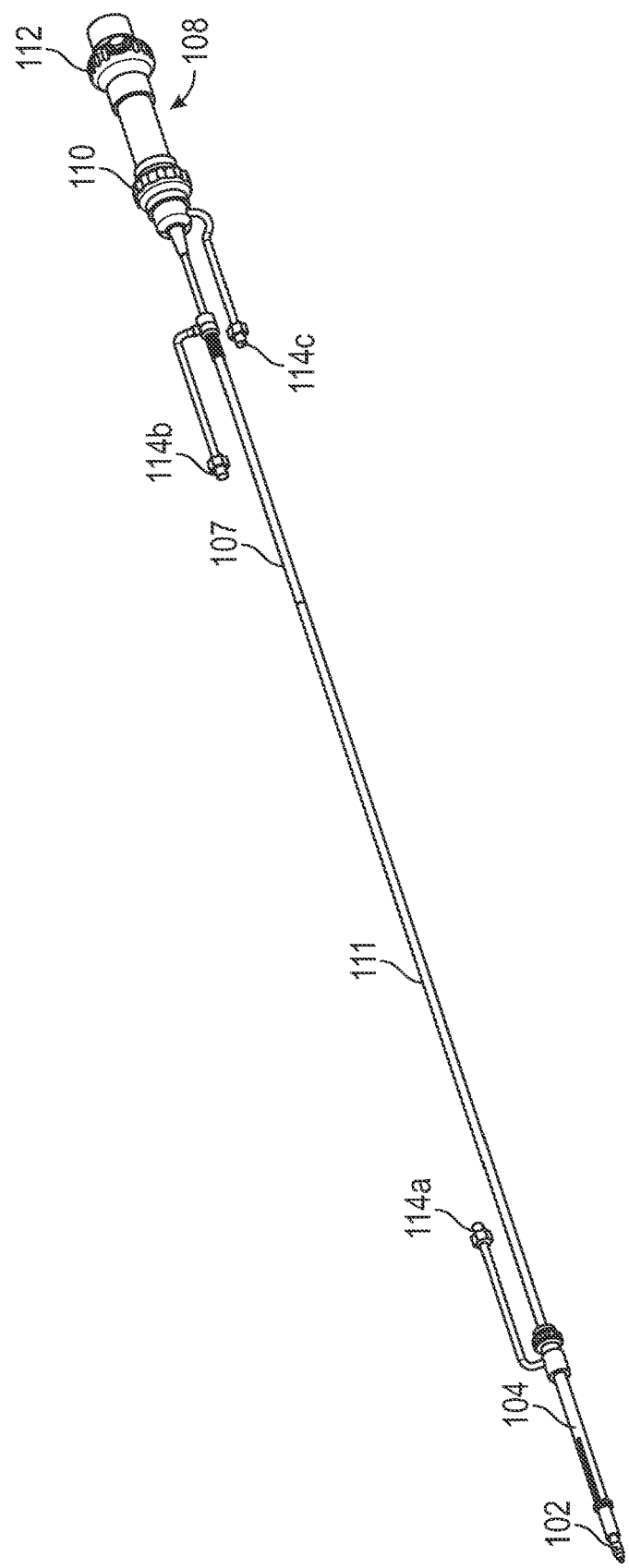
FIG. 1 illustrates a perspective view of a delivery system for delivering an implantable medical device (IMD) into a patient, according to an embodiment of the present disclosure.

FIG. 1 illustrates a perspective view of a delivery system 100 for delivering an IMD 102 into a patient, according to an embodiment of the present disclosure. The delivery system 100 may include an IMD sheath 104, a guide catheter 111, an introducer sheath 107, a handle 108, a deflection knob 110, a tether shuttle 112, and flush ports 114a, 114b, and 114c. The deflection knob 110 may be used to steer and guide the catheter 111 during implantation and/or removal of the IMD 102. The flush ports 114a, 114b, and 114c may be used to flush saline or other fluids through the catheter 111. The introducer sheath 107 may be advanced distally over the catheter 111 to provide additional steering and support for the catheter 111 during implantation and to surround the IMD 102 as it is introduced through a trocar or introducer into a patient.

Figure 2A:
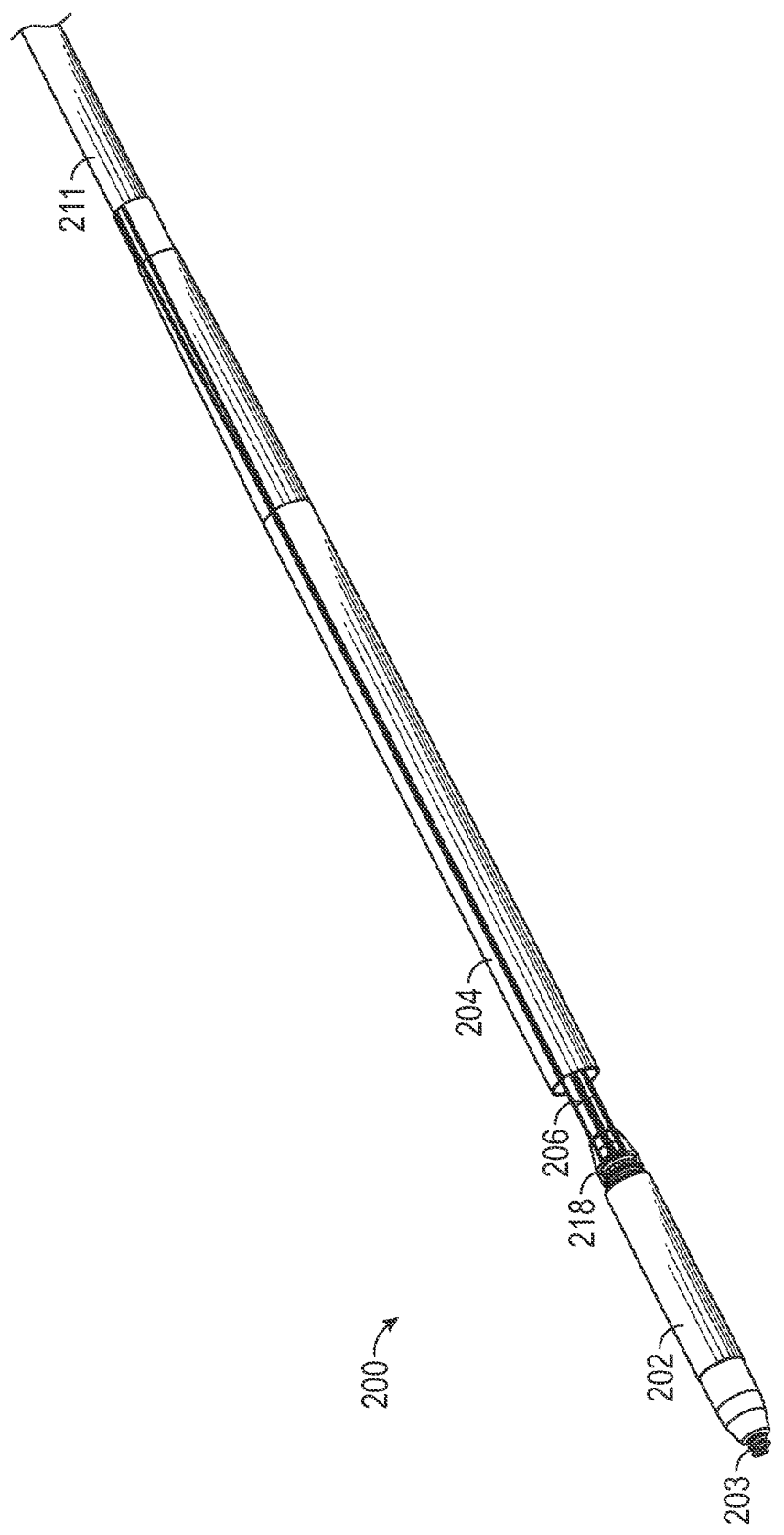
FIG. 2A illustrate a perspective view of a distal portion of a delivery system and an IMD, according to an embodiment of the present disclosure.

FIG. 2A illustrate a perspective view of a distal portion of a delivery system 200 and an IMD 202, according to an embodiment of the present disclosure. The IMD 202 may include a helix 203 that may be used to attach the IMD 202 to tissue of a patient. The IMD 202 may include an attachment member that is configured to removably connect to a docking cap 218 of a catheter 206. An IMD sheath 204 is shown pulled back proximally along the catheter 206 and a guide shaft 211 to expose the IMD 202 and the helix 203.

Figure 2B:
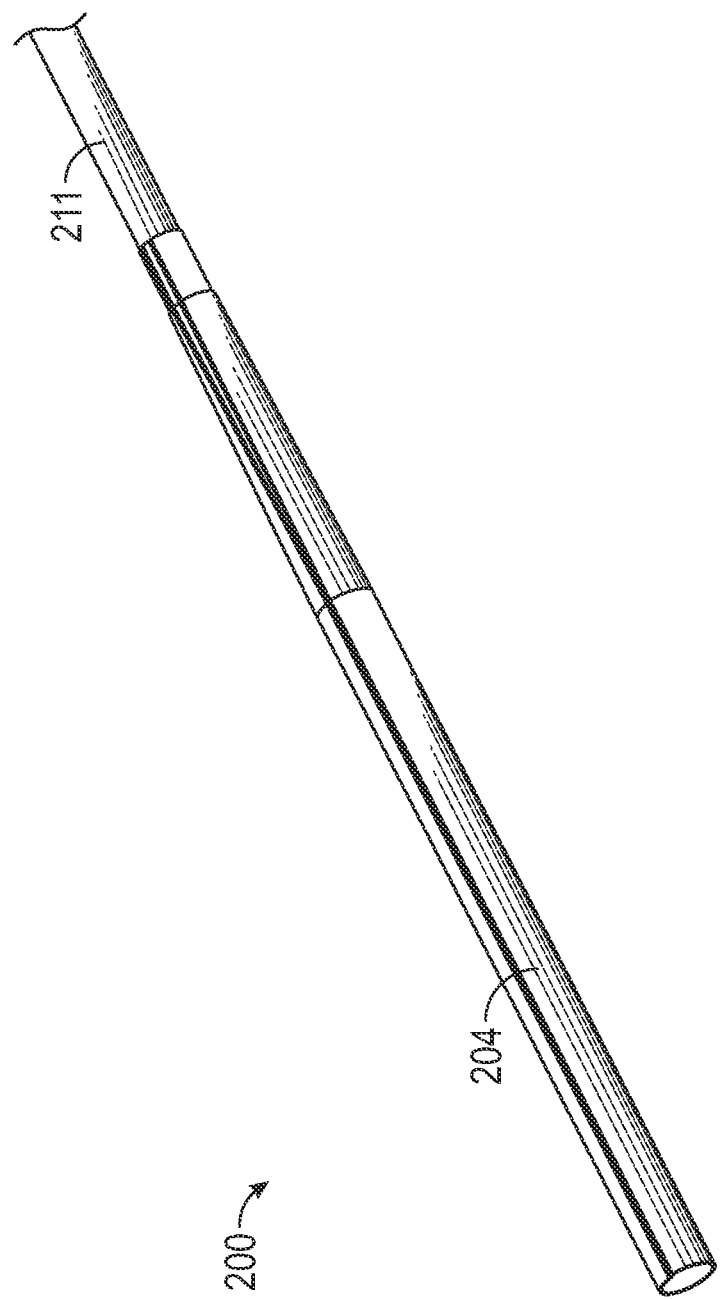
FIG. 2B illustrates a perspective view of an IMD sheath extended distally along a guide shaft, according to an embodiment of the present disclosure.

FIG. 2B illustrates a perspective view of the IMD sheath 204 extended distally along the guide shaft 211 to cover the catheter 206, the IMD 202, and the helix 203, according to an embodiment of the present disclosure. The extended IMD sheath 204 protects patient tissue from sharp edges of the helix 203 during implantation. Referring to FIGS. 2A and 2B, when the IMD sheath 204 is pulled back proximally, as shown in FIG. 2A, the IMD 202 is in an exposed, delivery configuration. When the IMD sheath 204 is advanced distally to protect the IMD 202 and the helix 203, as shown in FIG. 2B, the IMD 202 is in a protected, advancement configuration.

Figure 3A:
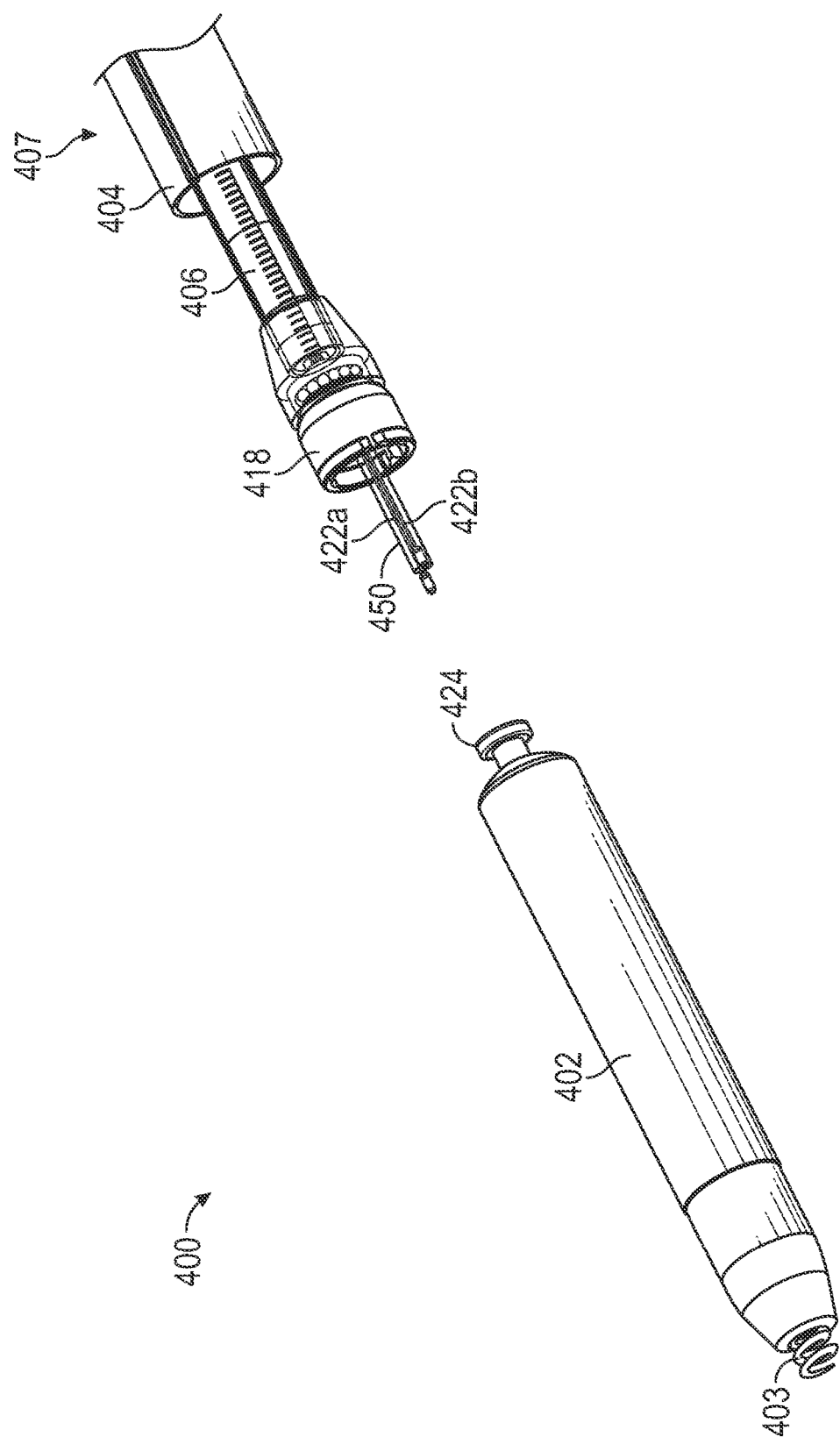
FIG. 3A illustrates a perspective view of a delivery system disconnected from an IMD, according to an embodiment of the present disclosure.

FIG. 3A illustrates a perspective view of a delivery system 400 disconnected from an IMD 402, according to an embodiment of the present disclosure. The delivery system 400 may include the IMD 402 when the IMD 402 is connected to the delivery system 400. The IMD 402 may include a helix 403 and an attachment member 424, such as a docking button, cap, stud, ridge, ledge, rim or the like.

The delivery system 400 may include a delivery catheter 407 that may include an IMD sheath 404, a catheter shaft 406, a docking cap 418, tethers 422a and 422b, and a restrainer 450 that extends outwardly from the catheter shaft 406 and surrounds at least portions of the tethers 422a and 422b. The restrainer 450 may be or include a flexible tube, lumen, cable, shaft, sleeve, sheath, or the like having an outer circumferential wall surrounding an interior passage into which at least portions of the tethers 422a and 422b may be retained.

Each tether 422a and 422b may include wires, shafts, tubes, cords, ropes, strings, or other similar structures that may extend throughout the restrainer 450, which, in turn, may extend through the catheter shaft 406. In at least one embodiment, the tethers 422a and 422b may include a shape memory material, such as nitinol. In other embodiments, the tethers 422a and 422b may include stainless steel wires or braids. As shown in FIG. 3A, the IMD 402 is disconnected from the docking cap 418 of the delivery catheter 407.

Figure 3B:
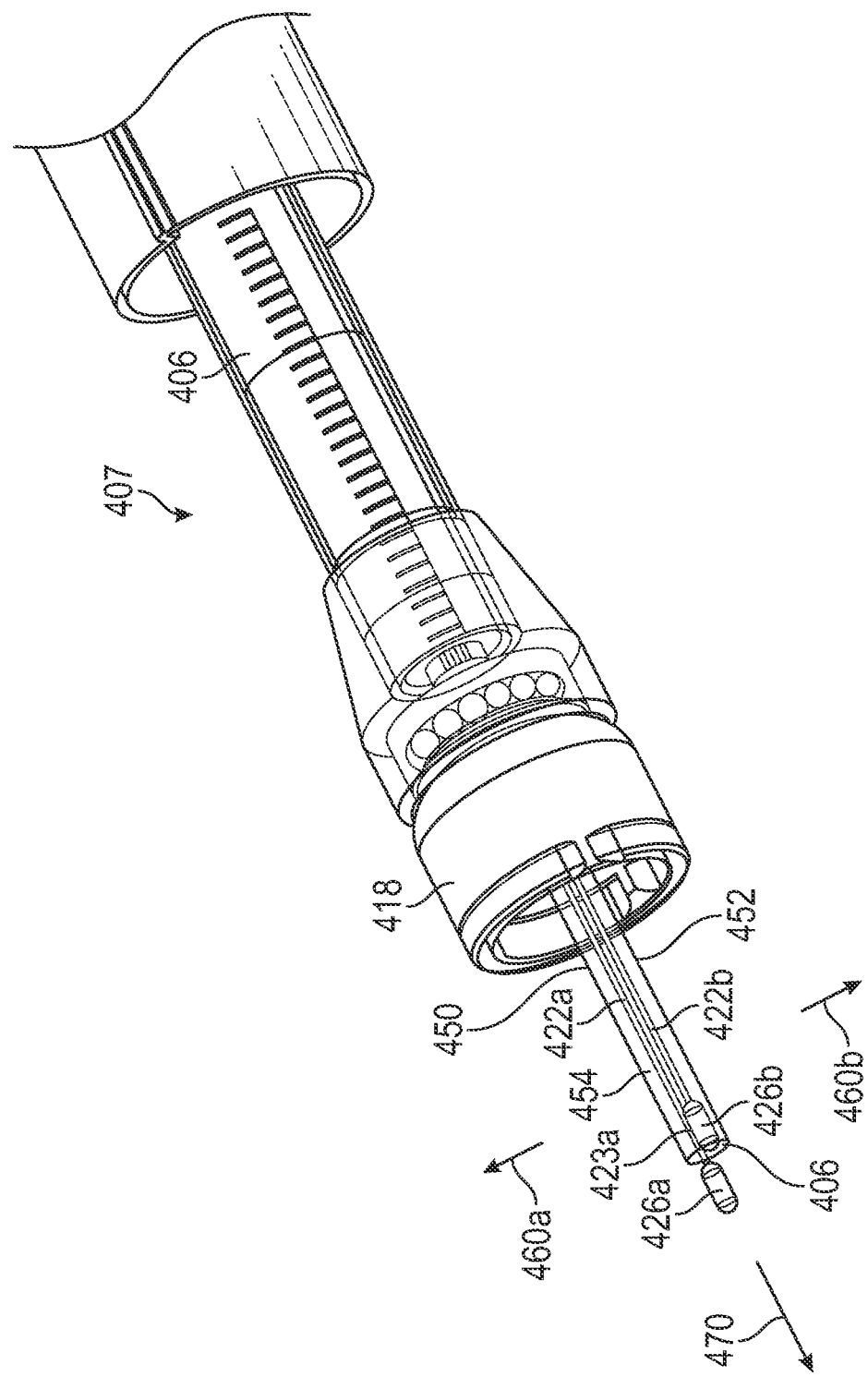
FIG. 3B illustrates a perspective view of a distal end of a delivery catheter with misaligned tethering members, according to an embodiment of the present disclosure.
Figure 3C:
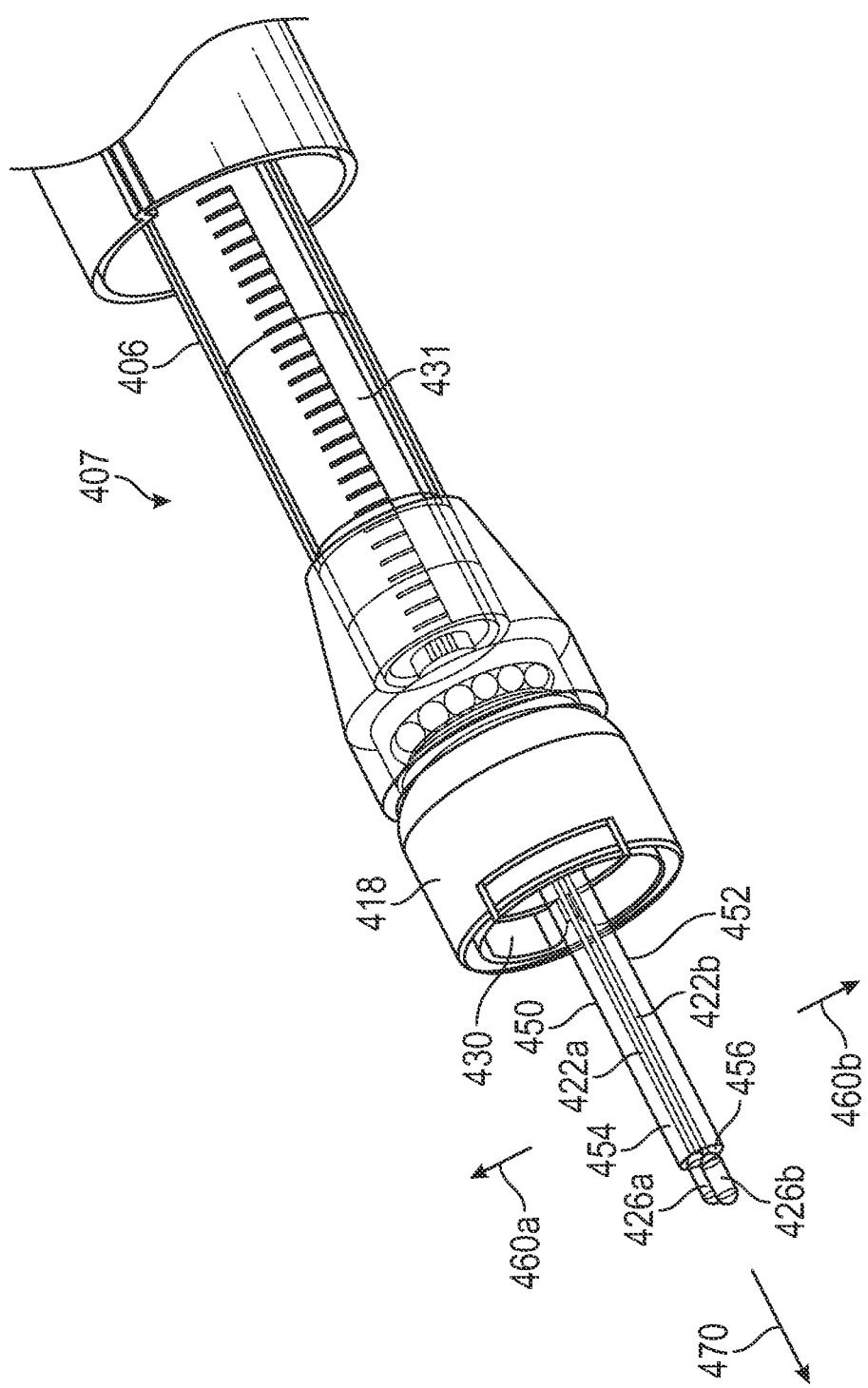
FIG. 3C illustrates a perspective view of a distal end of a delivery catheter with aligned tethering members, according to an embodiment of the present disclosure.

FIG. 3B illustrates a perspective view of a distal end of the delivery catheter 407 with mis- or unaligned tethering members 426a and 426b, according to an embodiment of the present disclosure. FIG. 3C illustrates a perspective view of the distal end of the delivery catheter 407 with aligned tethering members 426a and 426b, according to an embodiment of the present disclosure. Referring to FIGS. 3B and 3C, the tethers 422a and 422b may include the distal tethering members 426a and 426b. For example, the distal tethering members 426a and 426b may be or include expanded features on the tethers 422a and 422b that protrude radially therefrom, such as bumps, spheres, cylinders, blocks, or other similar shapes extending outwards from the tethers 422a and 422b. In at least one embodiment, each tethering member 426a and 426b may be expandable, such as a balloon, or other expandable mechanical structure. In general, the distal tethering members 426a and 426b may each have a cross sectional diameter that is larger than the cross sectional diameter of the tethers 422a and 422b or tethering lines thereof. In at least one embodiment, the tether 422a may be advanced further from the catheter 407 than tether 422b (as shown in FIG. 3B), so that when the tethers 422a and 422b are pushed together, the distal tethering member 426b rests against the tether 422a. As such, the combined cross sectional diameter of both distal tethering members 426a and 426b and the tethers 422a and 422b may be less than if the distal features were lined up side-by-side. The distal tethering members 426a and 426b may be configured to be moved between an aligned side-by-side orientation (as shown in FIG. 3C), and a mis- or unaligned orientation (as shown in FIG. 3B).

Referring to FIGS. 3A-3C, in order to connect the delivery catheter 407 to the IMD 402, the length of the tethers 422a and 422b, and thus the position of distal tethering members 426a and 426b, may be adjusted so that the distal tethering members 426a and 426b are not aligned in a side-by-side configuration.

As shown in FIGS. 3B and 3C, in particular, the restrainer 450 includes a flexible main longitudinal body 452, such as an outer shaft, that defines an internal passage 454 connected to a distal opening 456. The interior diameter of the internal passage 454 and the distal opening 456 may be greater than the combined diameter of the tethering members 426a and 426b in an aligned orientation. Alternatively, the interior diameter of the internal passage 454 may be large enough to contain a tethering member 426b aligned next to a tethering line 423a of the tether 422a. In the aligned orientation, both of the tethering members 426a and 426b may be fully extended out of the distal opening 456 of the restrainer 450, as shown in FIG. 3C The restrainer 450 restrains, constricts, or otherwise limits outward bowing, flexing, splaying, or other such movement of the tethers 422a and 422b away from one another in the directions of arrows 460a and 460b. For example, the restrainer 450 limits outward movement of the tether 422a in the direction of arrow 460a and the tether 422b in the direction of arrow 460b. As such, the restrainer 450 maintains the tethers 422a and 422b in close proximity to one another such that tethers 422a and 422b may remain generally aligned (such as being parallel) with an advancement or tethering direction 470 of the delivery catheter 407. Accordingly, the restrainer 450 protects against, or otherwise reduces the possibility of, the tethers 422a and 422b inadvertently releasing from the attachment member 424 of the IMD 402 (shown in FIG. 3A, for example).

The restrainer 450 may compress, squeeze, or otherwise force the tethers 422a and 422b together so that there is no clearance, gap, or the like therebetween. As such, the restrainer 450 may be formed of a resilient material, such as elastomeric material, that exerts a compressive force into the tethers 422a and 422b. Alternatively, the restrainer 450 may define a central passage 454 having a constant diameter throughout that allows the tethers 422a and 422b to move into and away from each other over short distances. The inner diameter of the outer wall 452 limits such movement. For example, a diametric clearance within the central passage 454 may be less than a diameter of a tethering member 426a or 426b, for example.

The restrainer 450 may squeeze, force, compress, or push the tethers 422a and 422b together or towards one another so that they remain aligned along a similar track, path, or the like. As such, the outstretched length of the tethers 422a and 422b relative to one another may remain constant (or substantially constant). The restrainer 450 minimizes or otherwise reduces tether splaying or separation during device deployment and implantation.

For the sake of clarity, the restrainer 450 is shown as being translucent, so that the tethers 422a and 422b are shown in the Figures. However, it is to be understood that the restrainer 450 may be shaded, opaque, or various colors, tints, hues, and the like.

Figure 3D:
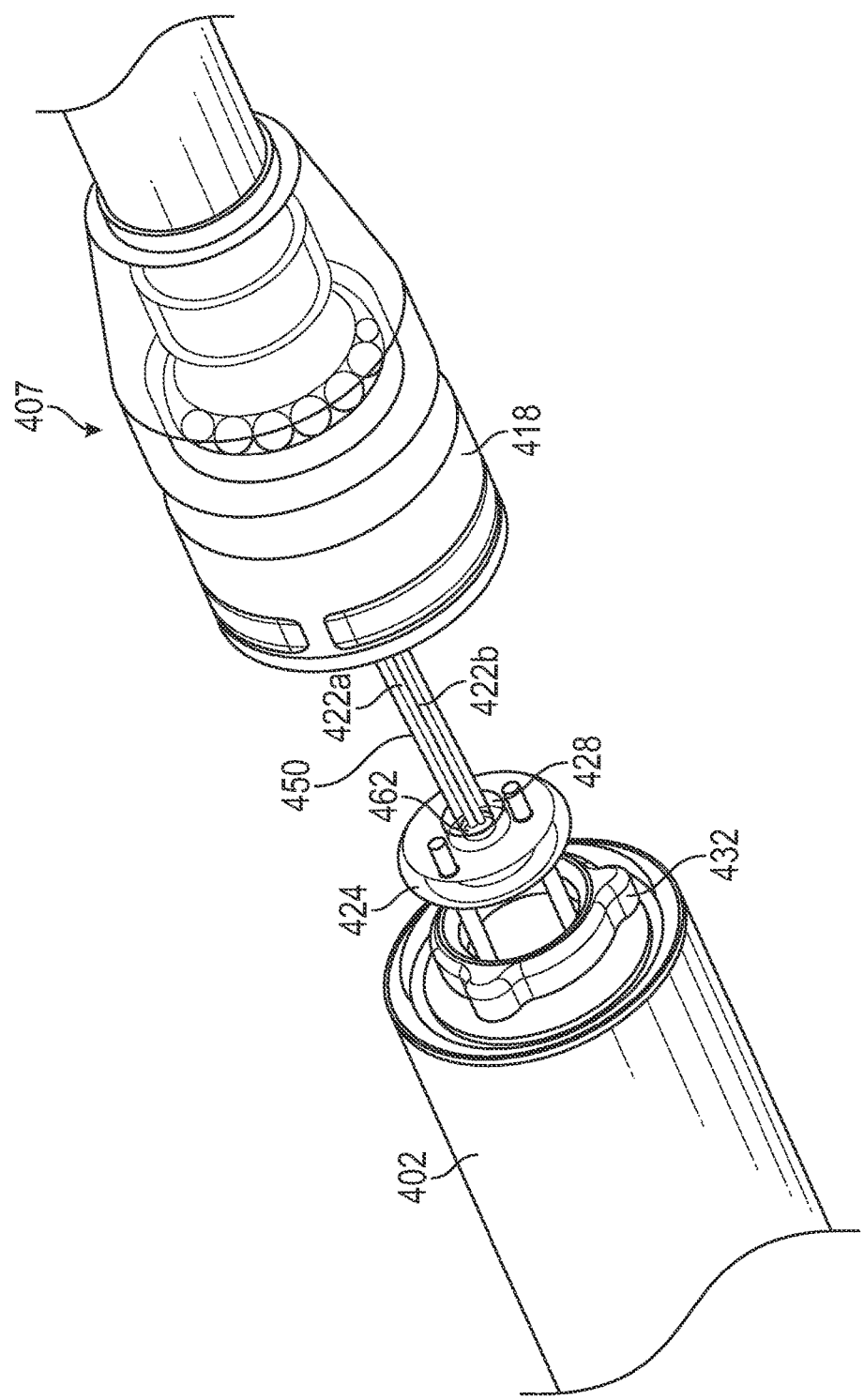
FIG. 3D illustrates a perspective view of a delivery catheter tethered to an IMD, according to an embodiment of the present disclosure.
Figure 3E:
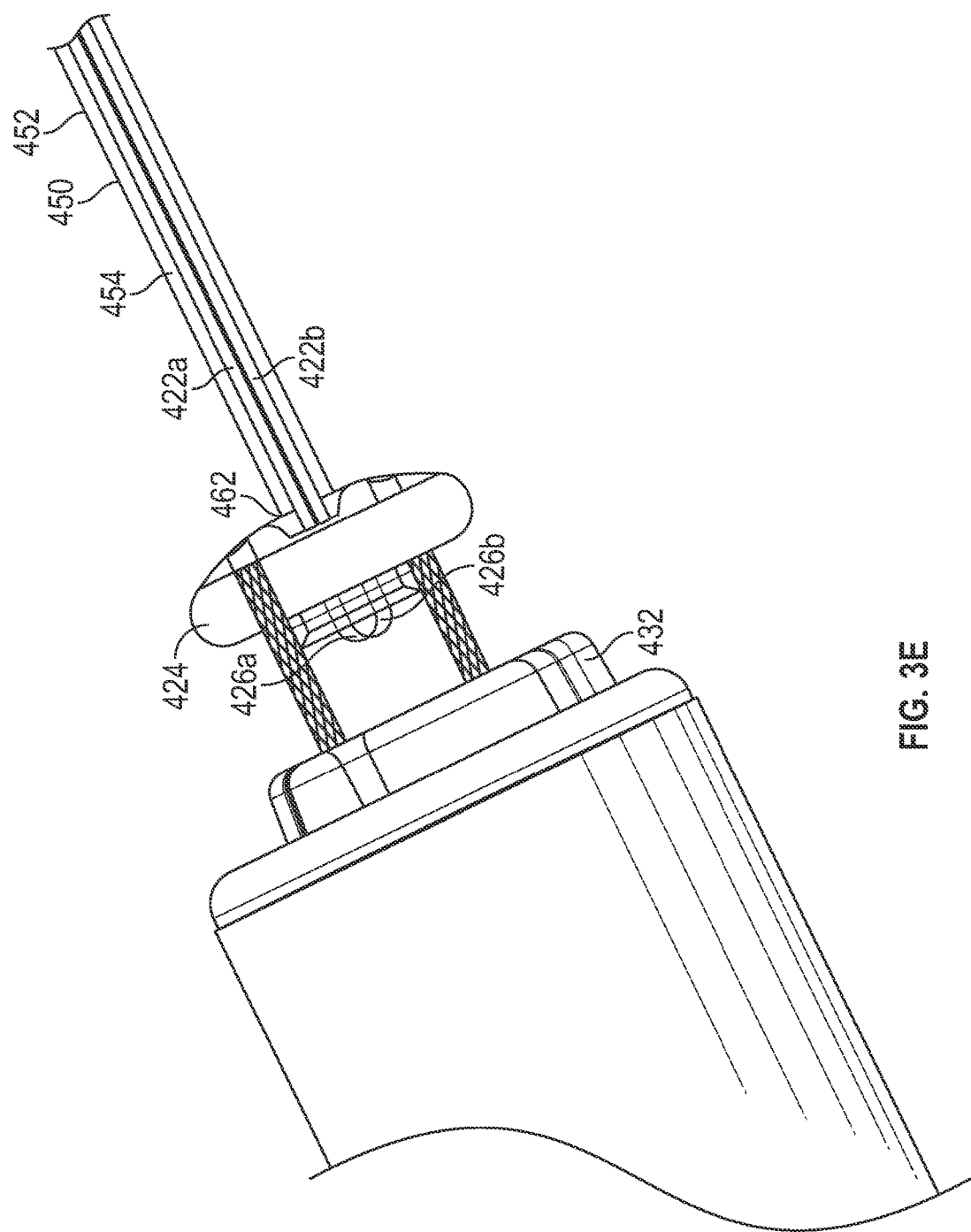
FIG. 3E illustrates a lateral view of a delivery catheter 407 tethered to an IMD, according to an embodiment of the present disclosure.

FIG. 3D illustrates a perspective view of the delivery catheter 407 tethered to the IMD 402, according to an embodiment of the present disclosure. FIG. 3E illustrates a lateral view of the delivery catheter 407 tethered to the IMD 402. Referring to FIGS. 3D and 3E, the distal tethering members 426a and 426b may be advanced into and through a hole 428 of the attachment member 424. The diameter of the hole 428 is large enough to allow the distal tethering members 426a and 426b of the tethers 422a and 422b to pass therethrough when in the misaligned configuration (as shown in FIGS. 3A and 3B). Upon passing the distal tethering members 426a and 426b through the hole 428, the length of the tethers 422a and 422b may then be adjusted to align the distal tethering members 426a and 426b in the side-by-side configuration. As such, the combined cross sectional diameter of the distal tethering members 426a and 426b becomes larger than the diameter of the hole 428, thereby locking the tethers 422a and 422b and distal tethering members 426a and 426b in the attachment member 424.

The distal end 462 of the restrainer 450 may not extend into the hole 428. Instead, the aligned tethering members 426a and 426b may extend outwardly from the distal opening 456, while the distal end 462 may abut into an outer surface of the attachment member 424 surrounding the hole 428. Optionally, the distal end 462 may be sized and shaped to also fit into the hole 428. For example, the distal end 426 of the restrainer 450 may pass into the hole 428, while the aligned tethering members 426a and 426b extend outwardly from the distal opening 456.

The docking cap 418 of the delivery catheter may include a torque slot that is sized and configured to mate with a torque key 432 located on a proximal end of the pacemaker IMD 402. The torque slot may be coupled to a torque shaft, which may run the length of the delivery catheter extending into the handle (not shown). The torque key may be a "male" key and the torque slot may be a "female" key, or vice versa. The torque key and the torque slot may include any number of shapes, such as square, rectangle, triangle, pentagon, hexagon, cross, "X", and the like, so long as the key fits within and can apply rotational torque to the slot. Once the tethers 422a and 422b are locked within the attachment member 424, the tethers 422a and 422b may be pulled proximally to pull the attachment member 424 and therefore the IMD 402 towards the delivery catheter 407 and to attach the IMD 402 to the delivery catheter 407, thereby engaging the torque slot with the torque key 432.

As described above, the tethers 422a and 422b may be used to tether the IMD 402 to the delivery catheter 407. The tethers 422a and 422b may be misaligned with respect to one another so that the distal tethering members 426a and 426b may fit through the hole 428 of the attachment member 424. Once misaligned, the tethers 422a and 422b may be removed from the attachment member 424 so that the IMD 402 releases from the delivery catheter 407. Connection and disconnection of the delivery catheter 407 from the IMD 402 may be further described in United States Patent Application Publication No. 2014/0074114, entitled "Delivery Catheter Systems and Methods," which is hereby incorporated by reference in its entirety.

Figure 4A:
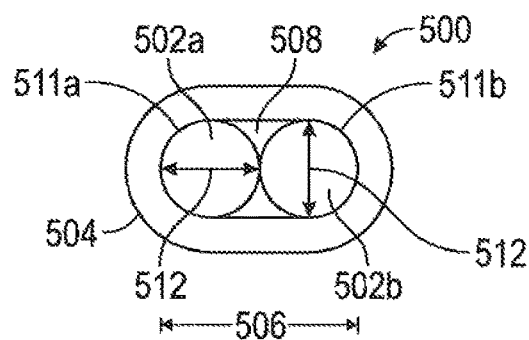
FIG. 4A illustrates an axial cross-sectional view of a restrainer retaining first and second tethers, according to an embodiment of the present disclosure.

FIG. 4A illustrates an axial cross-sectional view of a restrainer 500 retaining first and second tethering devices, such as tethers 502a and 502b, according to an embodiment of the present disclosure. The restrainer 500 includes a main body 504 defining a central passage 506. The diameter 508 of the central passage 506 may be large enough to accommodate both tethering members 511a and 511b of the tethers 502a and 502b, respectively, in an aligned, side-by-side orientation. For example, the diameter 508 of the central passage 506 may be larger than the combined diameters 512 and 512 of the tethering members 511a and 511b. As an example, if the diameters 512 and 512 are each 0.006", the diameter 508 may be 0.0125".

The main body 504 may be flexible, but may generally maintain the central passage 506 at one or more fixed diameters. For example, while the diameter 508 may be a first distance near a distal end of the restrainer 500, the diameter 508 may be a different distance near a proximal end of the restrainer 500, and/or at various other points between the proximal and distal ends. The main body 504 may not exert an inwardly-directed compressive force. Instead, the diameter 508 at various points along the restrainer 500 may generally be fixed, whether or not the diameter 508 is the same throughout the restrainer 500.

Figure 4B:
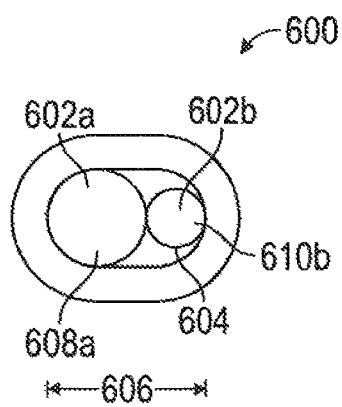
FIG. 4B illustrates an axial cross-sectional view of a restrainer retaining first and second tethers, according to an embodiment of the present disclosure.

FIG. 4B illustrates an axial cross-sectional view of a restrainer 600 retaining first and second tethers 602a and 602b, according to an embodiment of the present disclosure. As shown, a central passage 604 may have a diameter 606 that is larger than a combined diameter of a tethering member 608a of the first tether 602a and a tethering line 610b of the second tether 602b. Accordingly, aligned, side-by-side tethering members of the first and second tethers 602a and 602b may be too large to fit within the central passage 604

Figure 5:
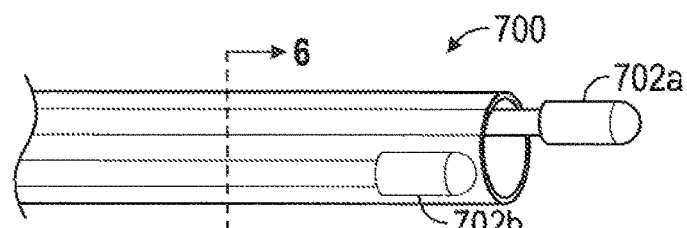
FIG. 5 illustrates a lateral view of a restrainer retaining first and second tethers in a misaligned orientation, according to an embodiment of the present disclosure.
Figure 6:
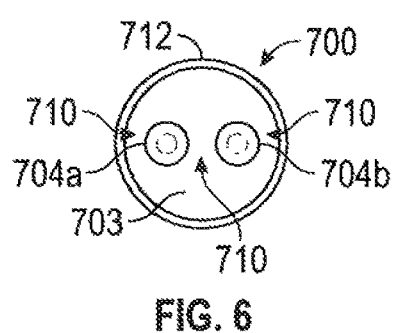
FIG. 6 illustrates a cross-sectional view of a restrainer retaining first and second tethers through line 6-6 of FIG. 5, according to an embodiment of the present disclosure.

FIG. 5 illustrates a lateral view of a restrainer 700 retaining first and second tethers 702a and 702b in a misaligned orientation, according to an embodiment of the present disclosure. FIG. 6 illustrates a cross-sectional view of the restrainer 700 retaining the first and second tethers 702a and 702b through line 6-6 of FIG. 5. Referring to FIGS. 5 and 6, a central passage 703 of the restrainer 700 may be sized and configured to provide a diametric clearance, gap, space, or area 710 between tethering lines 704a and 704b of the first and second tethers 702a and 702b. Accordingly, the first and second tethering lines 704a and 704 may shift toward and away from each other through the diametric clearance 710 within the central passage 703. The diametric clearance 710 is limited by the inner diameter of a main body 712 of the restrainer 700. The main body 712 may be sized to prevent the first and second tethering lines 704a and 704b from moving over distances greater than a diameter of a tethering member, such as the tethering members 511a and 511b shown in FIG. 4A, for example.

Figure 7:
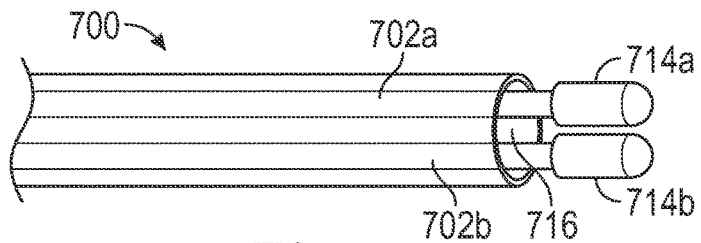
FIG. 7 illustrates a lateral view of a restrainer retaining first and second tethers in an aligned orientation, according to an embodiment of the present disclosure.

FIG. 7 illustrates a lateral view of the restrainer 700 retaining the first and second tethers 702a and 702b in an aligned orientation, according to an embodiment of the present disclosure. As shown, the tethering members 714a and 714b of the first and second tethers 702a and 702b are extended out of a distal opening 716 of the restrainer 700.

Figure 8:
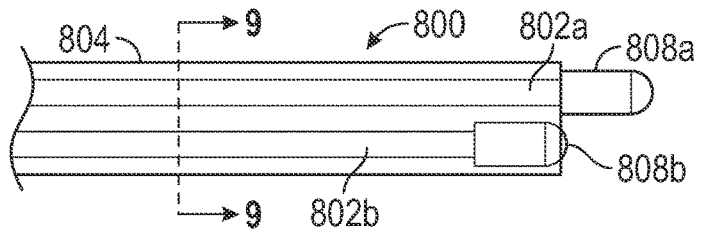
FIG. 8 illustrates a lateral view of a restrainer retaining first and second tethers in a misaligned orientation, according to an embodiment of the present disclosure.
Figure 9:
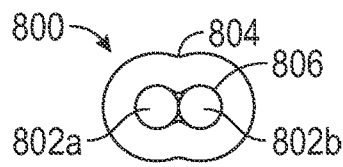
FIG. 9 illustrates a cross-sectional view of a restrainer retaining first and second tethers through line 9-9 of FIG. 8, according to an embodiment of the present disclosure.

FIG. 8 illustrates a lateral view of a restrainer 800 retaining first and second tethers 802a and 802b in a misaligned orientation, according to an embodiment of the present disclosure. FIG. 9 illustrates a cross-sectional view of the restrainer 800 retaining the first and second tethers 802a and 802b through line 9-9 of FIG. 8. The restrainer 800 may include a main body 804 that is formed of a flexible, resilient material that exerts an inwardly-directed compressive force. As such, the main body 804 may conform to outer surfaces of first and second tethers 802a and 802b and compress them into one another so that there is little or no clearance area, gap, or the like therebetween. Instead, as shown in FIG. 9, in particular, the first and second tethers 802a and 802 are slidably retained within a central passage 806 in which an inner diameter of the main body 804 that defines the central passage 806 compresses, clamps, or otherwise squeezes the first and second tethers 802a and 802b together and clings, sticks, or the like to the combined outer surface of the first and second tethers 802 and 802. Because the main body 804 is flexible and resilient, tethering members 808a and 808b may also be positioned within central passage 806 in misaligned and aligned positions.

Figure 10:
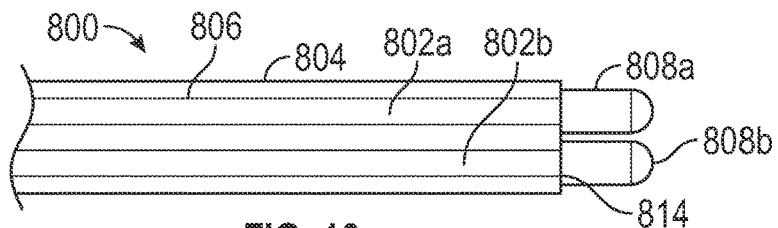
FIG. 10 illustrates a lateral view of a restrainer retaining first and second tethers in an aligned orientation, according to an embodiment of the present disclosure.

FIG. 10 illustrates a lateral view of the restrainer 800 retaining the first and second tethers 802a and 802b in an aligned orientation, according to an embodiment of the present disclosure. As shown, in the aligned position, the first and second tethering members 808a and 808b may extend outwardly from a distal opening 814 of the restrainer 800. Optionally, the aligned first and second tether members 808a and 808b may remain within the central passage 806 of the restrainer 800. The outer surface of the main body 804 of the restrainer 800 may be sized and shaped to fit through a hole of an attachment member, such as the attachment member 424 shown in FIGS. 3D and 3E.

Figure 11:
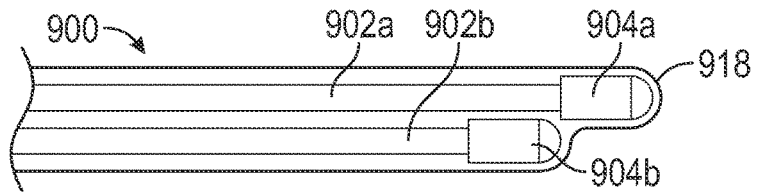
FIG. 11 illustrates a lateral view of a restrainer retaining first and second tethers in a misaligned orientation, according to an embodiment of the present disclosure.
Figure 12:
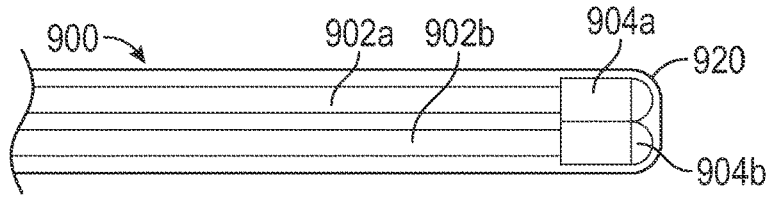
FIG. 12 illustrates a lateral view of a restrainer retaining first and second tethers in an aligned orientation, according to an embodiment of the present disclosure.

FIG. 11 illustrates a lateral view of a restrainer 900 retaining first and second tethers 902a and 902b in a misaligned orientation, according to an embodiment of the present disclosure. FIG. 12 illustrates a lateral view of the restrainer 900 retaining the first and second tethers 902a and 902b in an aligned orientation, according to an embodiment of the present disclosure. Referring to FIGS. 11 and 12, the restrainer 900 is similar to the restrainer 800 shown and described with respect to FIGS. 8-10, except that the restrainer 900 does not include a distal opening. Instead, the restrainer 900 encapsulates or otherwise covers the first and second tethers 902a and 902b, including the first and second tethering members 904a and 904b. In the misaligned orientation shown in FIG. 11, the restrainer 900 and the first and second tethers 902a and 902 are sized and shaped to fit through a hole of an attachment member. For example, the combined diameter of the distal end 918 is less than the diameter of the hole of the attachment member. In the aligned orientation shown in FIG. 12, an expanded distal aligned portion 920, including the restrainer 900, includes a combined diameter that exceeds that of the hole of the attachment member.

Figure 13:
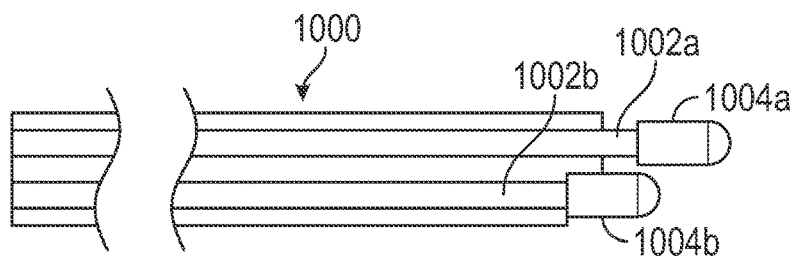
FIG. 13 illustrates a lateral view of a restrainer retaining first and second tethers, according to an embodiment of the present disclosure.

FIG. 13 illustrates a lateral view of a restrainer 1000 retaining first and second tethers 1002a and 1002b, according to an embodiment of the present disclosure. The restrainer 1000 may extend from a proximal end of the tethers 1002a and 1002b to areas proximate the distal tips of the tethers 1002 and 1002b. Optionally, the restrainer 1000 may extend over the tethering members 1004a and 1004b, such as shown and described in FIGS. 11 and 12. Any of the embodiments described above may include a restrainer that extends from proximal ends of tethers to areas proximate to or at distal ends.

Figure 14:
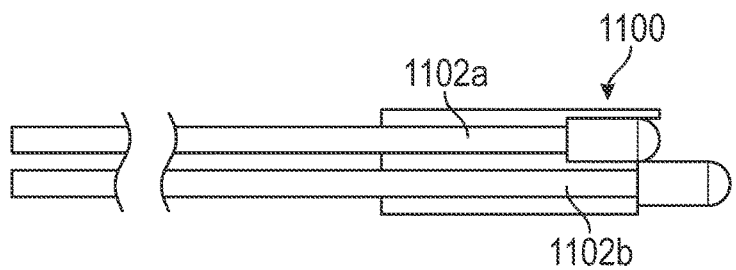
FIG. 14 illustrates a lateral view of a restrainer retaining first and second tethers, according to an embodiment of the present disclosure.

FIG. 14 illustrates a lateral view of a restrainer 1100 retaining first and second tethers 1102a and 1102b, according to an embodiment of the present disclosure. As shown, the restrainer 1100 may extend over distal portions of the tethers 1102 and 1102b, such as segments that are configured to extend outwardly from a catheter shaft 406, such as shown in FIGS. 3B and 3C. Embodiments of the present disclosure described above, such as shown in FIGS. 4-12, may include a restrainer sized as shown in FIG. 14.

Figure 15:
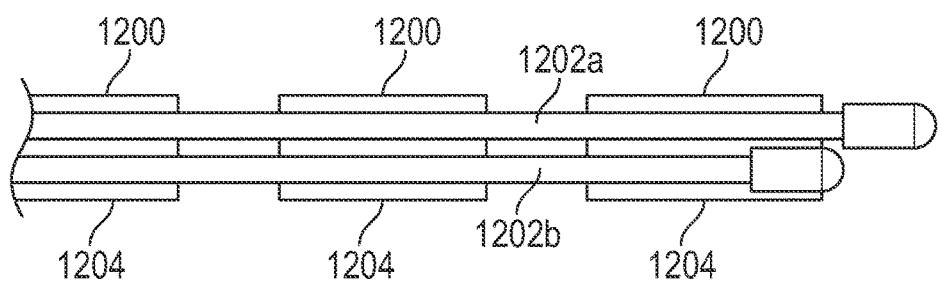
FIG. 15 illustrates a lateral view of a restrainer retaining first and second tethers, according to an embodiment of the present disclosure.

FIG. 15 illustrates a lateral view of a restrainer 1200 retaining first and second tethers 1202a and 1202b, according to an embodiment of the present disclosure. The restrainer 1200 may include separate and distinct segments 1204 positioned over a length of the tethers 1202a and 1202b. Embodiments of the present disclosure described above, such as shown in FIGS. 4-12, may include a restrainer configured as shown in FIG. 15.

Figure 16:
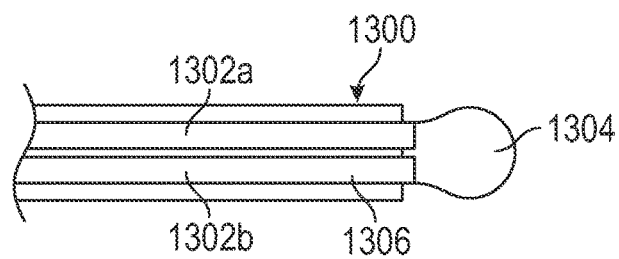
FIG. 16 illustrates a lateral view of a restrainer retaining first and second tethering devices, according to an embodiment of the present disclosure.

FIG. 16 illustrates a lateral view of a restrainer 1300 retaining first and second tethering devices 1302a and 1302b, according to an embodiment of the present disclosure. The restrainer 1300 may be positioned within a delivery catheter or catheter shaft, such as the catheter shaft 406 shown in FIGS. 38 and 3C, for example. The first tethering device 1302a includes a distal protuberance 1304, such as a sphere, block, pyramid, or the like, while the second tethering device 1302b includes a featureless, elongated distal segment 1306. The tethering devices 1302a and 1302b are further described in U.S. patent application Ser. No. 14/481,818 entitled "Systems and Methods for Implanting a Medical Device," filed Sep. 9, 2014, published as U.S. Pub. No. 20160067446, which is hereby incorporated by reference in its entirety. Any of the restrainers described in the present application may be used with tethering devices, such as those shown in FIG. 16.

Figure 17:
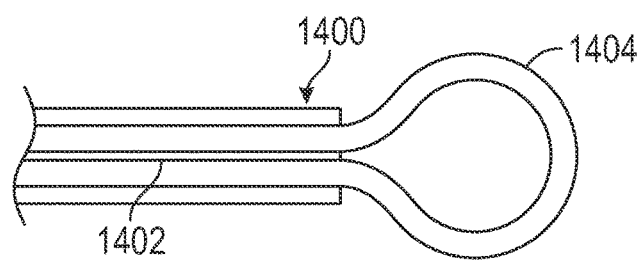
FIG. 17 illustrates a lateral view of a restrainer retaining a tethering device, according to an embodiment of the present disclosure.

FIG. 17 illustrates a lateral view of a restrainer 1400 retaining a tethering device 1402, according to an embodiment of the present disclosure. The restrainer 1400 may be positioned within a delivery catheter or catheter shaft, such as the catheter shaft 406 shown in FIGS. 38 and 3C, for example. The tethering device 1402 may be or include a tethering snare having an expandable loop 1404, such as described in in U.S. patent application Ser. No. 14/481,818 entitled "Systems and Methods for Implanting a Medical Device," filed Sep. 9, 2014 published as U.S. Pub. No. 20160067446, which is hereby incorporated by reference in its entirety. Any of the restrainers. Any of the restrainers described in the present application may be used with the tethering device 1402.

Referring to FIGS. 1-17, embodiments of the present disclosure provide restrainers that are configured to be positioned within delivery catheters or catheter shafts of an IMD delivery system. The restrainers are configured to prevent or otherwise limit outward bowing, splaying, or the like of tethering devices, such as the tethers shown in FIGS. 3A-15, and those shown and described with respect to FIGS. 16 and 17, for example.

Embodiments of the present disclosure provide restrainers that are configured to restrain, restrict, or otherwise limit movement of the tethering devices to intended translation movements (for example, intentional, desired movement to connect or disconnect an IMD with respect to a delivery catheter).

The restrainers described in the present application may be formed of various materials, such as elastomeric materials, latex, polymide, or other thin-walled tubing.

Embodiments of the present disclosure provide restrainers that may force, compress, squeeze, push, or otherwise move the tethering devices (or portions thereof) together or towards one another so that they remain aligned along a common track, path, or the like. The restrainers minimize or otherwise reduce tether splaying or separation during device deployment and implantation.

Additionally, embodiments of the present disclosure provide smooth release of the tethering devices, and eliminate, minimize, or otherwise reduce the possibility of the tethering devices entangling.

Figure 18:
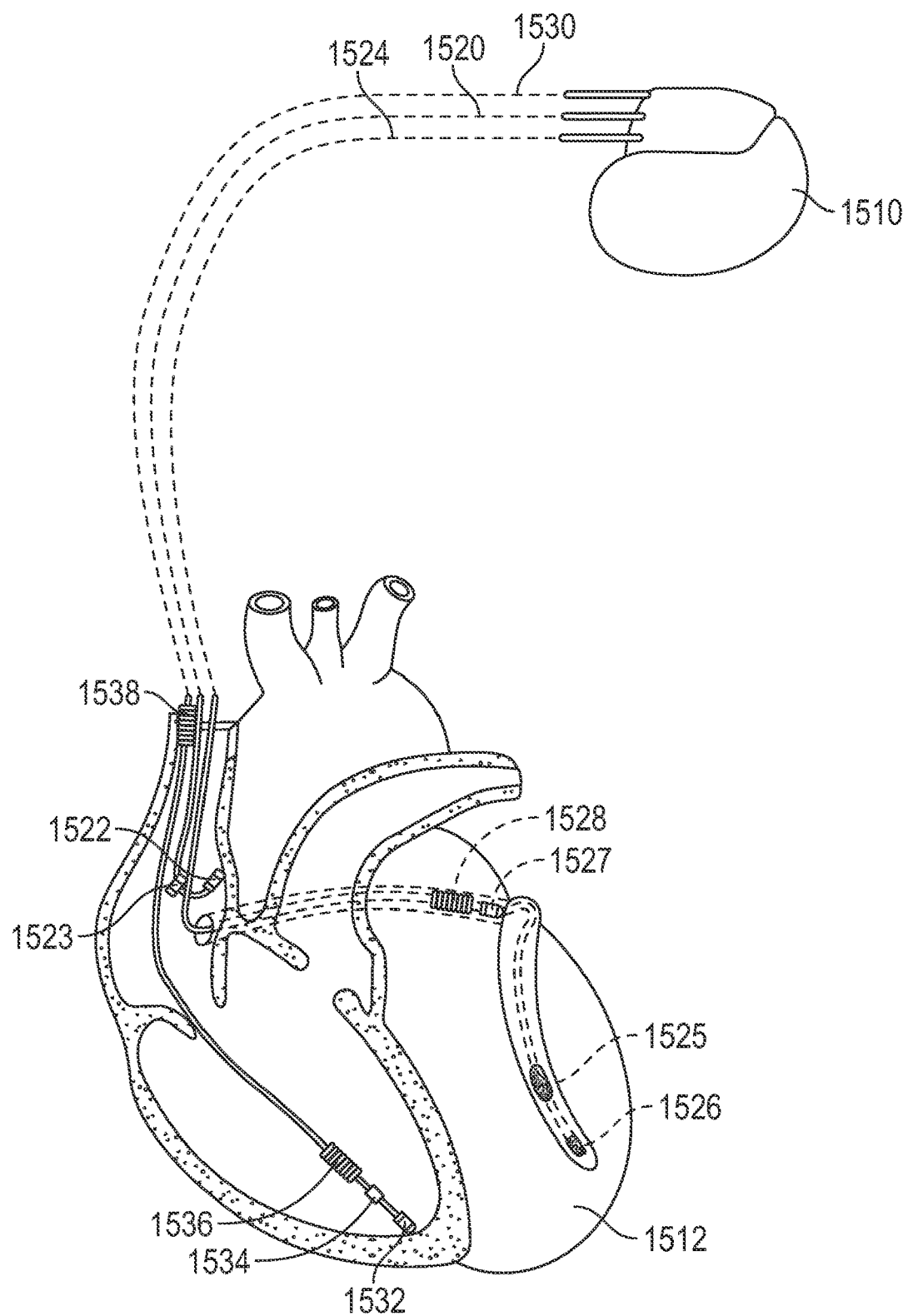
FIG. 18 illustrates a simplified view of an IMD in electrical communication with at least three leads implanted into a patient's heart, according to an embodiment.

FIG. 18 illustrates a simplified view of an IMD 1510 in electrical communication with at least three leads 1520, 1524, and 1530 implanted into a patient's heart 1512, according to an embodiment. The IMD 1510 may be implanted into the heart 1512 and released from a delivery catheter. The deliver catheter may include tethering devices restrained by any of the restrainers described above.

To sense atrial cardiac signals and to provide right atrial chamber stimulation therapy, the IMD 1510 may be coupled to an implantable right atrial lead 1520 including at least one atrial tip electrode 1522 that typically is implanted in the patient's right atrial appendage. The right atrial lead 1520 may also include an atrial ring electrode 1523 to allow bipolar stimulation or sensing in combination with the atrial tip electrode 1522.

To sense the left atrial and left ventricular cardiac signals and to provide left-chamber stimulation therapy, the IMD 1510 may be coupled to a lead 1524 designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the lead 1524 is designed to: receive atrial and/or ventricular cardiac signals; deliver left ventricular pacing therapy using at least one left ventricular tip electrode 1526 for unipolar configurations or in combination with left ventricular ring electrode 1525 for bipolar configurations; deliver left atrial pacing therapy using at least one left atrial ring electrode 1527 as well as shocking therapy using at least one left atrial coil electrode 1528.

The IMD 1510 is also shown in electrical communication with the patient's heart 1512 by way of an implantable right ventricular lead 1530 including, in the embodiment, a right ventricular (RV) tip electrode 1532, a right ventricular ring electrode 1534, a right ventricular coil electrode 1536, a superior vena cava (SVC) coil electrode 1538, and so on. Typically, the right ventricular lead 1530 is inserted transvenously into the heart 1512 so as to place the right ventricular tip electrode 1532 in the right ventricular apex such that the RV coil electrode 1536 is positioned in the right ventricle and the SVC coil electrode 1538 will be positioned in the right atrium and/or superior vena cava. Accordingly, the right ventricular lead 1530 is capable of receiving cardiac signals, and delivering stimulation in the form of pacing and shock therapy to the right ventricle.

The IMD 1510 may be one of various types of implantable devices, such as, for example, an implantable pacemaker, implantable cardioverter-defibrillator ("ICD"), defibrillator, cardiac rhythm management ("CRM") device, neurostimulator, electrophysiology ("EP") mapping and radio frequency ("RF") ablation system, or the like.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

The invention claimed is:

1. A system for implanting an implantable medical device (IMD) within a patient, the system comprising:
   an IMD comprising an attachment member; and
   a delivery catheter comprising:
      a sheath;
      a catheter shaft extendable outward from the sheath;
      a restrainer moveably positioned within the catheter shaft; and
      a plurality of tethering devices having at least a portion positioned within the restrainer, wherein the plurality of tethering devices are configured to removably tether to the attachment member of the IMD, and wherein the restrainer is configured to maintain the plurality of tethering devices in alignment with respect to one another along a delivery path of the delivery catheter to deliver the plurality of tethering devices to the attachment member of the IMD, wherein the plurality of tethering devices comprise first and second tethers having first and second distal tethering members, and wherein the restrainer comprises a central passage having a diametric clearance that is less than a diameter of the first or second distal tethering members.

2. The system of claim 1, wherein the restrainer exerts an inwardly-directed force into at least a portion of the plurality of tethering devices.

3. The system of claim 1, wherein the restrainer exerts a compressive force into at least a portion of the plurality of tethering devices.

4. The system of claim 1, wherein the restrainer encapsulates at least a distal portion of the plurality of tethering devices.

5. The system of claim 1, wherein the restrainer extends from a proximal end of the plurality of tethering devices to a distal end of the plurality of tethering devices.

6. The system of claim 1, a portion of the plurality of tethering devices configured to outwardly extend from the catheter shaft, wherein the restrainer is configured to extend over the portion of the plurality of tethering devices outwardly extending from the catheter shaft.

7. A system for implanting an implantable medical device (IMD) within a patient, the system comprising:
   an IMD comprising an attachment member; and
   a delivery catheter comprising:
      a plurality of tethering devices having at least a portion positioned within a restrainer, wherein the plurality of tethering devices are configured to removably tether to the attachment member of the IMD, and wherein the restrainer is configured to maintain the plurality of tethering devices in alignment with respect to one another along a delivery path of the delivery catheter to deliver the plurality of tethering devices to the attachment member of the IMD, wherein the plurality of tethering devices comprise first and second tethers having first and second distal tethering members, and wherein the restrainer comprises a central passage having a diametric clearance that is less than a diameter of the first or second distal tethering members.

8. A system for implanting an implantable medical device (IMD) within a patient, the system comprising:
a delivery catheter comprising:
a plurality of tethering devices having at least a portion positioned within a restrainer, wherein the plurality of tethering devices are configured to removably tether to an attachment member of the IMD, wherein the restrainer is configured to maintain the plurality of tethering devices in alignment with respect to each other along a delivery path of the delivery catheter to deliver the plurality of tethering devices to the attachment member of the IMD, and wherein the restrainer limits outward movement of the plurality of tethering devices in relation to the delivery path, wherein the restrainer comprises a main body having an inner diameter that defines a central passage, wherein at least a portion of the plurality of tethering devices is positioned within the central passage, wherein the plurality of tethering devices comprise first and second tethering members configured to secure to the attachment feature of the IMD, and wherein the central passage of the restrainer has a diametric clearance that is less than a diameter of the first or second distal tethering members.

9. The system of claim 8, wherein the restrainer exerts an inwardly-directed force into at least a portion of the plurality of tethering devices.

10. The system of claim 8, wherein the restrainer exerts a compressive force into at least a portion of the plurality of tethering devices.

11. The system of claim 8, wherein the restrainer encapsulates at least a distal portion of the plurality of tethering devices.

12. A system for implanting an implantable medical device (IMD) within a patient, the system comprising:
an IMD comprising an attachment member; and
a delivery catheter comprising:
(i) a sheath;
(ii) a catheter shaft extendable outward from the sheath;
(iii) a restrainer moveably positioned within the catheter shaft, wherein the restrainer comprises a main body having an inner diameter that defines a central passage, and
(iv) first and second tethers, wherein at least portions of the first and second tethers are positioned within the central passage, wherein the first and second tethers include first and second tethering members, wherein at least one of the first and second tethers is configured to be moved between a first orientation in which the first tethering member is misaligned with respect to the second tethering member, and a second orientation in which the first tethering member is aligned with respect to the second tethering member, wherein the first and second tethers are configured to removably tether to the attachment member of the IMD, wherein the restrainer is configured to maintain the first and second tethers in alignment along a common path, and wherein the restrainer limits outward movement of the first and second tethers in relation to the common path, and wherein the first and second tethering members are configured to secure to the attachment feature of the IMD, and wherein the central passage of the restrainer has a diametric clearance that is less than a diameter of the first or second distal tethering members.

13. The system of claim 12, wherein the restrainer exerts an inwardly-directed force into at least a portion of the first and second tethers.

14. A system for implanting an implantable medical device (IMD) within a patient, the system comprising:
a delivery catheter comprising:
a sheath;
a catheter shaft extendable outward from the sheath;
a restrainer moveably positioned within the catheter shaft; and
at least one tethering device having at least a portion positioned within the restrainer, wherein the at least one tethering device is configured to removably tether to an attachment member of the IMD, wherein the restrainer is configured to maintain the at least one tethering device in alignment along a delivery path of the delivery catheter to deliver the at least one tethering device to the attachment member of the IMD, and wherein the restrainer limits outward movement of the at least one tethering device in relation to the delivery path, wherein the at least one tethering device comprises at least two tethering devices having at least a portion positioned within the restrainer, wherein the at least two tethering devices are configured to removably tether to an attachment member of the IMD, wherein the restrainer comprises a main body having an inner diameter that defines a central passage, wherein at least a portion of the at least two tethering devices is positioned within the central passage, wherein the at least two tethering devices comprise at least a first and a second distal tethering member configured to secure to the attachment feature of the IMD, and wherein the central passage of the restrainer has a diametric clearance that is less than a diameter of the first or the second distal tethering members.

* * * * *